US012616729B2

(12) United States Patent
Kodama et al.

(10) Patent No.: US 12,616,729 B2
(45) Date of Patent: May 5, 2026

(54) PSYLLIUM HUSK GRANULE, METHOD FOR PRODUCING SAME, AND POWDERED DRINK CONTAINING PSYLLIUM HUSK GRANULE

(71) Applicant: NISSIN FOODS HOLDINGS CO., LTD., Osaka (JP)

(72) Inventors: Shoki Kodama, Osaka (JP); Nobuko Inoike, Osaka (JP); Takato Shimizu, Osaka (JP)

(73) Assignee: NISSIN FOODS HOLDINGS CO., LTD., Osaka (JP)

( * ) Notice: Subject to any disclaimer, the term of this patent is extended or adjusted under 35 U.S.C. 154(b) by 765 days.

(21) Appl. No.: 17/759,017

(22) PCT Filed: Feb. 8, 2021

(86) PCT No.: PCT/JP2021/004595

§ 371 (c)(1),
(2) Date: Jul. 18, 2022

(87) PCT Pub. No.: WO2021/192663

PCT Pub. Date: Sep. 30, 2021

(65) Prior Publication Data

US 2023/0044477 A1      Feb. 9, 2023

(30) Foreign Application Priority Data

| Mar. 25, 2020 | (JP) | ................................ | 2020-053483 |
| Jul. 15, 2020 | (JP) | ................................ | 2020-120996 |
| Jan. 28, 2021 | (JP) | ................................ | 2021-011598 |

(51) Int. Cl.

| *A61K 36/68* | (2006.01) |
| *A23L 2/39* | (2006.01) |
| *A23L 2/60* | (2006.01) |
| *A23L 33/22* | (2016.01) |
| *A23P 10/20* | (2016.01) |

(52) U.S. Cl.
CPC ................ *A61K 36/68* (2013.01); *A23L 2/39* (2013.01); *A23L 2/60* (2013.01); *A23L 33/22* (2016.08); *A23P 10/20* (2016.08); *A23V 2002/00* (2013.01); *A61K 2236/15* (2013.01)

(58) Field of Classification Search
CPC ..... A61K 36/68; A61K 2236/15; A23P 10/20; A23L 33/22; A23L 2/39; A23L 2/60; A23V 2002/00
See application file for complete search history.

(56) References Cited

U.S. PATENT DOCUMENTS

| 5,149,541 | A |   | 9/1992 | Leis, Jr. et al. |
| 5,338,549 | A | * | 8/1994 | Hord ....................... A23L 33/21 |
|  |  |  |  | 424/490 |
| 5,445,831 | A |   | 8/1995 | Leis, Jr. et al. |
| 5,910,317 | A |   | 6/1999 | Broaddus |
| 6,210,722 | B1 |   | 4/2001 | Wullschleger et al. |
| 6,221,421 | B1 |   | 4/2001 | Wullschleger et al. |
| 2001/0051203 | A1 |   | 12/2001 | Ueda et al. |
| 2004/0156927 | A1 |   | 8/2004 | Ueda et al. |
| 2014/0335123 | A1 |   | 11/2014 | Pak |
| 2018/0179604 | A1 |   | 6/2018 | Kim et al. |
| 2019/0224124 | A1 |   | 7/2019 | Williams |

FOREIGN PATENT DOCUMENTS

| CN | 103960593 |   | 8/2014 |
| CN | 105231199 |   | 1/2016 |
| CN | 105519651 |   | 4/2016 |
| CN | 105796662 |   | 7/2016 |
| CN | 107823144 | * | 3/2018 |
| CN | 108272087 |   | 7/2018 |
| CN | 109789217 |   | 5/2019 |
| EP | 0362926 | * | 4/1990 |
| JP | H02-200167 |   | 8/1990 |
| JP | 108-504593 |   | 5/1996 |
| JP | H109-154527 |   | 6/1997 |
| JP | 2001-103934 |   | 4/2001 |
| JP | 2001-522614 |   | 11/2001 |
| JP | 2003-002836 |   | 1/2003 |
| JP | 2006-158333 |   | 6/2006 |
| JP | 2015-212258 |   | 11/2015 |
| JP | 2016-190801 |   | 11/2016 |
| JP | 2018-514233 |   | 6/2018 |
| JP | 2018-153151 |   | 10/2018 |

OTHER PUBLICATIONS

Engineering Department (2006) pp. 1-2.*
Sandberg (May 18, 2017).*
International Search Report and Written Opinion of PCT/JP2021/004595, date of mailing: Apr. 6, 2021, 11 pages Including English translation of the International Search Report.
Clinical and Testing, Approach to Pathology (vol. 33)—Introduction of measuring assay of remnant lipoprotein (RLP-C)-, Fukuoka City Medical Association Clinical Examination Center, 2007, 2 pages, available at: http://www.city.fukuoka.med.or.jp/kensa/ensinbunri/enshin_37_x.pdf; English translation provided.

(Continued)

*Primary Examiner* — Shirley V Gembeh

(74) *Attorney, Agent, or Firm* — HSML P.C.

(57) ABSTRACT

The purpose of the present invention is to provide a psyllium husk granule whose affinity for water is significantly improved, and a method for producing the psyllium husk granule. In addition, the purpose of the present invention is to provide a powdered drink in which the psyllium husk granule is used. The psyllium husk granule is obtained by performing granulation using powdered sugar which has passed through a 120 to 280-mesh Tyler screen. The method for producing the psyllium husk granule comprises fluidizing a mixture containing a psyllium husk and powdered sugar which has passed through a 120 to 280-mesh Tyler screen, then spraying water, and finally drying the mixture for granulation.

3 Claims, No Drawings

(56) References Cited

OTHER PUBLICATIONS

Davidson M.H. et al., "Long-term effects of consuming foods containing psyllium seed husk on serum lipids in subjects with hypercholesterolemia", Am. J. Clin. Nutr., 1998, vol. 67, No. 3, pp. 367-376.

Ohta A. et al., "Effect of Ezetimibe Monotherapy on Low-Density Lipoprotein Cholesterol and on Markers of Cholesterol Synthesis and Absorption in Japanese Patients with Hypercholesterolemia.", J. Clin. Med. Res., 2017, vol. 9, No. 6, pp. 476-481.

Inoike N. et al., Effect of Psyllium Husk on the Suppression of Postprandial Elevation of Serum Triglyceride Level in Human—A Randomized, Double-blinded, Placebo-controlled, Crossover study-, Jpn. Pharmacol. Ther., Sep. 20, 2019, vol. 47, No. 9, pp. 1537-1543.

International Search Report and Written Opinion of PCT/JP2020/ 033225, Oct. 27, 2020, 11 pages including English translation of the International Search Report.

Office Action issued for Chinese Patent Application No. 202080023633. 8, Jan. 17, 2024, 15 pages including machine translation.

EatRight, "Psyllium Husk Should Be Taken at Higher Dose with Sufficient Water to Maximize Its Efficacy", Journal of the Academy of Nutrition and Dietitics, 2017 (EatRight).

Chinese Office Action issued in Chinese Application No. 202080023633. 8, dated Apr. 23, 2024, 14 pages, English machine translation provided.

Leaf Lean et al., "Diagnosis and Treatment of Dyslipidemia (2nd ed.)", Personism's Military Health Press, published Dec. 31, 2013, 7 pages, cited in Chinese Office Action, partial English translation provided.

Yang Jianfeng et al., "Family Nutrition Complete Book", Jangxi Science and Technology Press, dated Apr. 30, 2015, 5 pages, cited in Chinese Office Action, partial English translation provided.

Cutfield, et al., "Psyllium Supplementation in Adolescents Improves Fat Distribution & Lipid Profile: A Randomized, ParticipantBlinded, Placebo-Controlled, Crossover Trial", Jul. 2012 | vol. 7 | Issue 7 |e41735 (Cutfield).

Pankaj Garg, "Psyllium Husk Should Be Taken at Higher ose with Sufficient Water to Maximize Its Efficacy", Journal of the Academy of Nutrition and Dietetics, p. 681, 2017 (Garg).

Jenkins et al, "Effect on Blood Lipids of Very High Intakes of Fiber In Diets Low in Saturated Fat and Cholesterol", New England Journal of Medicine, vol. 329, No. 1, p. 21-26, 1993 (Jenkins).

* cited by examiner

PSYLLIUM HUSK GRANULE, METHOD
FOR PRODUCING SAME, AND POWDERED
DRINK CONTAINING PSYLLIUM HUSK
GRANULE

TECHNICAL FIELD

The present invention relates to a psyllium husk granule, and a method for producing the psyllium husk granule. More specifically, the present invention relates to a psyllium husk-containing composition whose affinity for water is improved.

BACKGROUND ART

In recent years, the intake of dietary fiber has decreased with the change in dietary habit. In Dietary Reference intakes for Japanese (2015 edition), the tentative dietary goal for preventing life-style related diseases in intake of dietary fiber is 19 g or more for an adult male and 17 g or more for an adult female. However, according to National Health and Nutrition Examination Survey in 2017, the daily intake of dietary fiber per adult human was 15.2 g for a male and 14.8 g for a female, showing that the tentative dietary goal for preventing life-style related diseases was not attained.

The tentative dietary goal for preventing life-style related diseases in intake of dietary fiber has been established because there have been many reports that insufficient intake of dietary fiber is associated with the onset of lifestyle related diseases. Dietary fiber is known to have an effect such as an intestinal regulation action, and it is also known that the intestinal regulation action is positively correlated with water retentivity. Thus, incorporation of dietary fiber-enriched food into the regular diet may be beneficial for persons who suffer from constipation or diarrhea due to bad dietary habits, westernized dietary habits, increased stress and the like.

Examples of the supply source for ingestion of dietary fiber include psyllium husks. In general, a psyllium husk is dissolved in water and ingested. However, addition of water to a psyllium husk is likely to form an undissolved lumps of powder (lump). Since the surface of the undissolved lump of powder is hydrated to turn into a gel, the undissolved lump of powder is difficult to crush once it is formed. Therefore, dispersion of a psyllium husk in an aqueous solution requires that a container with a lid be charged with water and the psyllium husk and vigorously shaken, or the contents of the container be stirring by apparatus such as a magnetic stirrer. Thus, it can be hardly said that a psyllium husk is easily ingested.

SUMMARY OF INVENTION

Technical Problem

On the other hand, there have appeared commercial products whose dispersibility is advertised to be improved by applying various measures such as granulation so that a psyllium husk-containing composition is even slightly more easily dispersed in water. However, these commercial products may be somewhat improved as compared to conventional products, but is not dramatically improved. Therefore, a psyllium husk granule whose dispersibility in water is further improved is strongly desired.

An object of the invention of the present application is to provide a psyllium husk granule whose affinity for water is significantly improved.

Solution to Problem

For solving the above-described problem, the present invention provides a psyllium husk granule obtained by performing granulation using powdered sugar which has passed through a 120 to 280-mesh Tyler screen. A powdered drink is preferable in which the granule is used. Here, the 120 to 280-mesh Tyler screen corresponds to a screen aperture size of 53 to 125 μm as calculated on the basis of JIS. Therefore, the grain size of powdered sugar which has passed through the 120 to 280-mesh Tyler screen is equivalent to 53 to 125 μm. The same applies hereinafter.

According to such a configuration, affinity for water can be significantly improved by performing granulation using powdered sugar having a small grain size. The good affinity for water results in excellent dispersibility, so that the psyllium husk granule can be easily used as a powdered drink.

For solving the above-described problem, the present invention provides a method for producing a psyllium husk granule, the method comprising fluidizing a mixture containing a psyllium husk and powdered sugar which has passed through a 120 to 280-mesh Tyler screen, then spraying water, and finally drying the mixture for granulation.

According to such a configuration, a psyllium husk granule whose hydrophilicity is improved can be easily produced with existing equipment only by changing the grain size of powdered sugar.

Advantageous Effects of Invention

According to the present invention, a psyllium husk granule whose affinity for water is significantly improved can be obtained by performing granulation using powdered sugar having a small grain size. Since the affinity for water is improved, the psyllium husk granule can be dispersed in an aqueous solution without using a shaker. This enables a psyllium husk to be easily ingested as long as water is available.

DESCRIPTION OF EMBODIMENTS

Hereinafter, a preferred embodiment for carrying out the present invention will be described.
<Psyllium Husk>
The psyllium husk is a dietary fiber material containing as its main component a polysaccharide having a highly branched structure. Examples of the psyllium husk for use in the present invention include husks obtained from seeds of *Plantago ovata* which is a plant of the family Plantaginaceae, or ground products thereof. Here, examples of the psyllium husk or ground product thereof include those that are commercially available as Psyllium, Psyllium Husk, Psyllium Husk Powder, Psyllium Seed Gum, Isagol and the like (hereinafter, referred to as "psyllium husk powder"). There is no limitation on the particle size and grade of the psyllium husk powder for use in the present invention, and psyllium husk powder having little contaminants and a high purity is preferable.

The psyllium husk is highly safe and tasteless and odorless, and is therefore easy to ingest continuously over a long period of time. In the present invention, it is preferable to ingest the psyllium husk as a granule or a powdered drink.

In granulation, various nutrients, various vitamins, minerals, dietary fiber and various additives may be further blended if necessary.

EXAMPLE

The present invention will be described in detail on the basis of Example. In Example, glassware meeting Japanese Industrial Standard was used.
<Psyllium Hulk Granule>

Example

In the present embodiment, 42 kg of a psyllium husk was mixed with 1.5 kg of powdered sugar which had passed through a 120 to 280-mesh Tyler screen. Next, the mixture was put in a fluidized bed granulator, and granulated with water. In this way, a psyllium husk granule was obtained.

Comparative Example

The same procedure as in Example was carried out except that as granulated sugar below 120 mesh, i.e. granulated sugar which had passed through the screen, one having a grain size of more than 125 μm was used.
<Test for Examination of Affinity for Water>
A test for examination of affinity for water was conducted in the following manner.

First, an aqueous pigment blue No. 1 at a concentration of 0.01 wt % was prepared. Next, 180 mL of the aqueous pigment blue thus prepared and a 3 cm-long stirrer were put in a 300 ml beaker, and the beaker was set on a magnetic stirrer. Subsequently, using a stainless stand and a cramp, a 50 mL tube was set so as to locate an opening at a height of 8 cm from a water level. The opening of the tube was turned up, and a psyllium husk granule was put into the tube. Here, the amount of the psyllium husk granule put into the tube was set so that the content of psyllium husk-derived dietary fiber was 3.6 g. The opening was closed by an aluminum foil, and the stirrer bar was rotated at 100 rpm. The tube was rotated by 180 degrees, and the psyllium husk granule was dropped into the beaker with one end of the aluminum lid fixed to the tube. After the dropping, the mixture was stirred for 30 seconds, the rotation of the stirrer bar was then stopped, and a surface of the beaker in plan view was photographed by a camera. The photographed image was converted to a gray scale using image analysis software Image J, the area value of the surface of the beaker and the area value of a non-precipitating powder portion were determined, and the ratio of the non-precipitating powder portion to the surface of the beaker was calculated.

Here, while an aqueous pigment blue No. 1 was used in the present embodiment, the pigment was used for the purpose of nothing more than facilitating discrimination from the psyllium husk in image analysis. Therefore, the color of the pigment is not particularly limited and may be red or green as long as it is a color which facilitates discrimination from the psyllium husk. The aqueous pigment was used at ordinary temperature (23±2 degrees).

For Example and Comparative Example, measurements were made by the test method described above. The test was conducted five times, and the average value was calculated. Table 1 shows the results.

TABLE 1

| | First | Second | Third | Fourth | Fifth | Average |
|---|---|---|---|---|---|---|
| Example | 15% | 13% | 10% | 12% | 11% | 12.2% |
| Comparative Example | 52% | 42% | 55% | 57% | 55% | 52.2% |

It is obvious from Table 1 that for each sample, there is substantially no test method-dependent variation because the numerical values in the tests are similar. Therefore, the difference between the numerical values in Example and Comparative Example, in which the same psyllium husk was used, may be a numerical value showing the extent to which hydrophilicity was improved by modification. That is, it was indicated that reduction of the grain size of powdered sugar enabled improvement of affinity for water.

As described above, according to the present invention, affinity for water can be significantly improved by using powdered sugar which has passed through a 120 to 280-mesh Tyler screen. This results in good dispersibility in water, so that the psyllium husk can be easily ingested.

The invention claimed is:

1. A psyllium husk granule obtained by performing granulation using powdered sugar, wherein the powdered sugar has passed through a 120 to 280-mesh Tyler screen prior to the granulation, thereby providing a dispersibility of the psyllium husk granule in water that is greater than a dispersibility of a psyllium husk granule prepared using powdered sugar having a particle size larger than a size corresponding to a 120-mesh Tyler screen.

2. A powdered drink comprising the psyllium husk granule according to claim 1.

3. A method for producing a psyllium husk granule, the method comprising:

fluidizing a mixture containing a psyllium husk and powdered sugar that has passed through a 120 to 280-mesh Tyler screen; then spraying water to the resulting mixture; and then drying the mixture, thereby the psyllium husk granule being formed, wherein a dispersibility of the psyllium husk granule in water is greater than a dispersibility of a psyllium husk granule prepared using powdered sugar having a particle size outside the 120 to 280-mesh Tyler screen range.

* * * * *